Figure 1A:
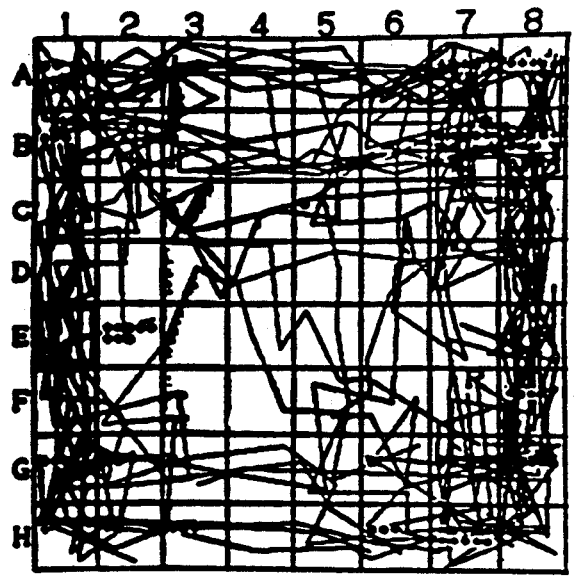

United States Patent [19]

Cacabelos

[11] Patent Number: 4,939,124
[45] Date of Patent: Jul. 3, 1990

[54] TREATMENT AND DIAGNOSIS OF DEMENTIA

[75] Inventor: Ramón Cacabelos, Santiago de Compostela, Spain

[73] Assignee: Laboratorios Serono S.A., Spain

[21] Appl. No.: 148,667

[22] Filed: Jan. 26, 1988

[51] Int. Cl.⁵ ...................... A61K 37/36; G01N 33/74
[52] U.S. Cl. .......................................... 514/12; 514/2; 514/879; 436/63; 436/811
[58] Field of Search ..................... 514/14, 12, 16, 806, 514/2, 879; 436/63, 811

[56] References Cited

U.S. PATENT DOCUMENTS

| | | | |
|---|---|---|---|
| 4,622,312 | 11/1986 | Felix et al. | 514/12 |
| 4,727,041 | 2/1988 | Aroonsakul | 436/87 |
| 4,728,638 | 3/1988 | Bauer et al. | 514/11 |
| 4,791,099 | 12/1988 | Aroonsakul | 514/2 |

OTHER PUBLICATIONS

Reubi et al., Cited in Chem. Abstracts, vol. 102: 191161k (1985).
GHRH-Induced GH Response in Patients with Senile Dementia of the Alzheimer Type, Ramon Cacabelos, Acta Endocrinologica (Copenh) 1988, 117: 295-301.

Primary Examiner—Jacqueline Stone
Attorney, Agent, or Firm—Ostrolenk, Faber, Gerb & Soffen

[57] ABSTRACT

The administration of Somatostatin and growth hormone releasing factor at useful dosage levels alleviates the symptoms of various neuropsychiatric disorders.

Growth hormone and neuropsychiatric responses to the administration of growth hormone releasing factor to mammals indicate its usefulness as an antemortem marker for senile dementia of the Alzheimer's type.

4 Claims, 6 Drawing Sheets

EFFECTS OF SOMATOSTATIN AND GRF ON BEHAVIOR
(SN8M-MAZE)

NEUTRAL POSITION

SHOCK POSITION

—— C
---- SS
·········· GRF

TREATMENT AND DIAGNOSIS OF DEMENTIA

The invention deals with methods for treating somatotropinergic deficiencies via the use of SS and/or GRF. Thus, pharmaceutical compositions containing one or more of SS and GRF are administered via various routes to effect improvements in various physiological and psychological disorders.

The invention also deals with the use of GRF as a marker for SDAT.

BACKGROUND

The somatotropinergic system (STS) is the only neuroendocrine axis in which specific stimulatory and inhibitory neuropeptidergic regulators have been demonstrated thus far. In normal conditions, growth hormone-releasing factor (GRF) and somatostatin (SS) are the hypothalamic hypophysiotropic hormones responsible for the regulation of growth hormone (GH) secretion.

At the same time, GRF and SS are influenced by central mono-aminergic and peptidergic neuromodulators to optimize the functioning of the STS. See Cacabelos R., Niigawa H., Hariguchi S. "Hypothalamohypophyseal system and brain function." J. Clin. Sci. 22:1108-1120 (1986).

Recent investigations suggest that the functional structure of the STS characteristically represented at the peripheral level might exist in the central nervous system (CNS). Furthermore, SS levels are reduced in specific areas of the CNS in patients with senile dementia and are elevated in the neostriatum of patients with Huntington's chorea. See Cacabelos R., Niigawa H., Ikemura Y. "Neuroendocrine correlates in senile dementia of the Alzheimer type. "Progr. Clin. Neurosci. 2:231-247 (1986); Beal M. F., Uhl G., Mazurek M. F., Kowall N., Martin J. B. "Somatostatin: Alterations in the central nervous system in neurological diseases." in: Martin J. B., Barchas J. D., Ed. Neuropeptides in neurologic and psychiatric disease. pp. 215-257 (Raven Press, N.Y., 1986); Epelbaum J. "Somatostatin in the central nervous system: physiology and pathological modifications." Progr. Neurobiol. 27:63-100 (1986). In addition, an abnormal rise of GH in response to GnRH or TRH has been described in several neuropsychiatric disorders. See in Brown G. M., Koslow S. M., Reichlin S. Ed. Neuroendocrinology and psychiatric disorder (Raven Press, N.Y., 1984). It has been speculated that the central regulators of the STS (e.g., GRF, SS) influence higher activities of the CNS. Such speculation led to search for potential therapeutic uses of these neuropeptides in those neurological diseases in which the normal functioning of the STS is impaired.

The neurochemical characteristics of early and late onset senile dementia of the Alzheimer type (SDAT) can be clearly demonstrated in postmortem studies in which it is possible to observe that cholinergic and somatostatinergic deficits are more pronounced in patients with an early onset of the disease. See Rossor M. N., Iversen L. L., Reynolds G. P., Mountjoy C. Q., Roth M. "Neurochemical characteristics of early and late onset types of Alzheimer's disease." Br. Med. J. 288:961-964 (1984). In advanced stages, clinical assessments show that the course of the disease is more rapid and prominent in younger patients.

Since dementia may be attributed to various etiologies of which SDAT accounts for at least 50% of the cases, the search for antemortem markers capable of establishing an early differential diagnosis for identifying potentially reversible or treatable causes of dementia is becoming an extremely important matter.

SDAT is believed to be a multisystem disorder. See Price D. L., Struble R. G., Whitehouse P. J., Kitt C. A., Cork L. C., Walker L. C., Casanova M. F. "Alzheimer's disease: A multisystem disorder. "in: Martin J. B., Barchas J. D., (Ed). Neuropeptides in neurologic and psychiatric disease. pp. 209-214 (Raven Press, N.Y., 1986). The most relevant peptidergic abnormalities in SDAT involve a clear deficit in cortical somatostatin and corticotropin-releasing factor (CRF). Other peptidergic and monoaminergic systems are also affected.

THE INVENTION

It has been discovered that growth hormone releasing factor (GRF) and somatostatin (SS) when administered together or separately, can treat neuropsychiatric disorders in some mammals. Specifically either or both exert significant effects on locomotor activity and improve learning abilities. It has also been found that the GRF-induced GH response can be taken as a useful marker for the early stages of SDAT.

PEPTIDES

Various commercially available forms of SS and GRF can be employed in the invention. Biologically active fragments can be substituted for all or part of the SS or GRF used. Somatostatin is generally characterized as growth hormone-releasing inhibiting factor. It is compound No. 8561 in Merck Index, 10th ed. (1983). It is preferred that the 1-14 fragment (i.e., SS-14) be employed herein. Various commercial products containing useful forms of SS may be used herein. Mixtures are operable.

Growth hormone releasing factor is chemically describable as the stimulatory growth-hormone releasing factor of the hypothalamus that assists in the nueroregulation of growth hormone secretion. It is compound No. 4416 in Merck Index, 10th ed. (1983). Preferred for use herein are the segments or fragments designated as 1-44 and 1-29. Various commercial products containing useful forms may be used herein. Mixtures are operable.

DOSAGES

Pharmaceutical preparations used in accordance with the invention will contain one or more active substances including at least one of SS and GRF along with the optional inclusion of pharmaceutically acceptable carrier(s). Peptide levels of about 1 to about 10 mcg/kg body weight i.v. and of about 5 to about 50 mcg/kg body weight s.c. are operable. The length of time for which the SS and/or GRF-containing composition is administered can vary greatly. Depending upon the effect desired, daily administration may be preferred. Administration every 6 or 12 hours can also be used. Useful times of administration depend upon the preferences of the treating physician.

IN THE DRAWINGS:

FIG. 1

Computer recordings of behavioral patterns of rats treated with somatostatin and growth hormone-releasing factor in a maze paradigm.

A. Behavioral pattern of prototype control rat (5 mcg 0.9% saline, i.c.v.) in a maze paradigm.

B. Behavioral pattern of a rat treated with somatostatin (SS-14; 1 mcg, i.c.v.).

C. Behavioral pattern of a rat treated with growth hormone-releasing factor (GRF$_{1-44}$; 1 mcg, i.c.v.).

D. Behavioral pattern of a rat treated with GRF$_{1-44}$ (5 mcg, i.c.v.).

The animals had to learn to escape from the shock area in order to avoid a continuous 1.5 mA electric shock. Experimental time —30 minutes.

FIG. 2(A–F)

Effects of somatostatin and GRF on locomotor activity and learning in a maze paradigm.

The rats were treated intracerebroventricularly with SS-14 (1 mcg) and GRF$_{1-44}$ (1 mcg) and their behavior was automatically recorded by computer using the maze paradigm shown in FIG. 1. p/t denotes pulses per time unit (minute). Locomotor activity was quantified in pulses per minute or cm$^2$/min. Total inputs (I/O) in neutral position (white bars) and shock position (black bars) denote how many times the animals enter neutral and shock areas. The N/S ratio results from dividing I/O in neutral position by I/O in shock position and is interpreted as an index of learning in the 30-minute experimental period. The positional time (seconds) represents how long the animals stay in neutral (white bars) or shock (black bars) areas. N-sp and S-sp (in seconds) indicate the time-latency per movement or input in neutral (white bars) and shock (black bars) areas, respectively.

● $p < 0.005$ vs C (control)
■ $p < 0.005$ (NA vs SA)

FIG. 3

It shows GRF-induced GH response in elderly subjects (●) and patients with early (■) and late onset senile dementia of the Alzheimer type (▲).

\* $p < 0.005$ vs. basal level (0) (means ±SD)
\*\* $p < 0.005$ vs. control (●).

FIG. 4

It illustrates the correlation between the GRF-induced GH response 60 minutes after injection and the mental performance of patients with early onset senile dementia of the Alzheimer type 24 hours prior to testing. The following Examples illustrate the invention.

EXAMPLE 1

To clarify whether SS and GRF display at the central level the same antagonistic effect that they have at the pituitary level, the effects of these neuropeptides on several behavioral parameters have been studied using the OUCEM-86$^{TM}$ (Osaka University Computerized Electronic Maze). The system is integrated by the following components: a Programmable Electronic Platform (PEP) (620×620 mm) equipped with 48 photo beam sensors (OPX-T30); a Programming Panel (PP) (Model BECM-0064) for paradigm stimulation; a Shock Generator Scrambler (SGS) (Model BSG-1065) to apply continuous or discontinuous electric current to the PEP; a Control Station (CS) (BEC 16-Bio Computer Control Station BCS-1105; Bio Medica, Ltd., Osaka) which processes inputs/outputs as an interface device to automatically computerize behavioral parameters; and a Computer System (NEC PC-9801 VM2) with 1 megabyte Random Access Memory (RAM) for data processing and experimental setting.

Male Wistar rats (175-200 g) (N =5-8 rats/group) received intracerebroventricular (i.c.v.) injections of GRF$_{1-44}$ and SS-14 over a range of 0.1 to 10 mcg. Then the rats were studied in the OUCEM under two different paradigms (e.g., open field and maze paradigms).

The animals were placed in the PEP for 30-minute periods and locomotor activity (LA) was automatically recorded in an open field paradigm. Total LA is represented as total inputs (I/O) including movements in four-footed position (4F) and in two-footed position (2F), grooming, rearing and jumping activity, while linear (horizontal) movements (4F) are represented as pulses per minute (pm) or cm$^2$/min.

The i.c.v. administration of SS (1 mcg) provoked quantitative and qualitative changes with a significant decrease in LA (31.16±6.90 pm vs 20.88±2.82 pm, t=3.08, $p<0.02$) while GRF (1 mcg) induced a hyperkinetic syndrome characterized by compulsive, uncontrolled movements with an LA rate of 47.60±5.35 pm (t=4.21, $p<0.005$)(control = 1122±248 cm$^2$/min; GRF = 1713.6±69.5 cm$^2$/min., t = 18.73, $p<0.005$). These changes were dose-dependent (SS:ED$_{50}$ = 1.83 nmol, E$_{max}$=6.10 nmol; GRF$_{1.44}$ ED$_{50}$=99.1 pmol, E$_{max}$=1.98 nmol; GRF1-29:ED$_{50}$=297 pmol, E$_{max}$=5.95 nmol).

EXAMPLE 2

This example shows the effects of the intracerebroventricular administration of SS and GRF on locomotor activity and learning in a maze paradigm.

Figure 1B:
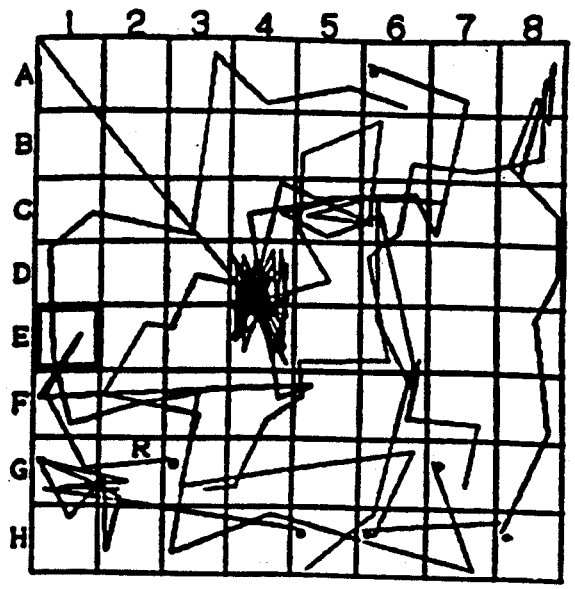
Figure 1C:
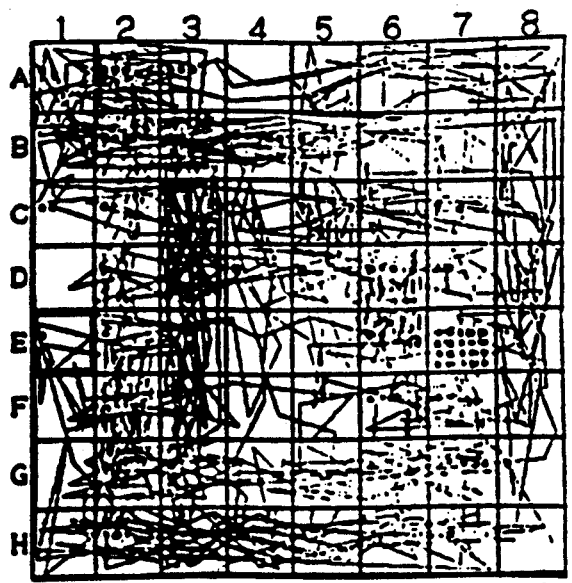
Figure 1D:
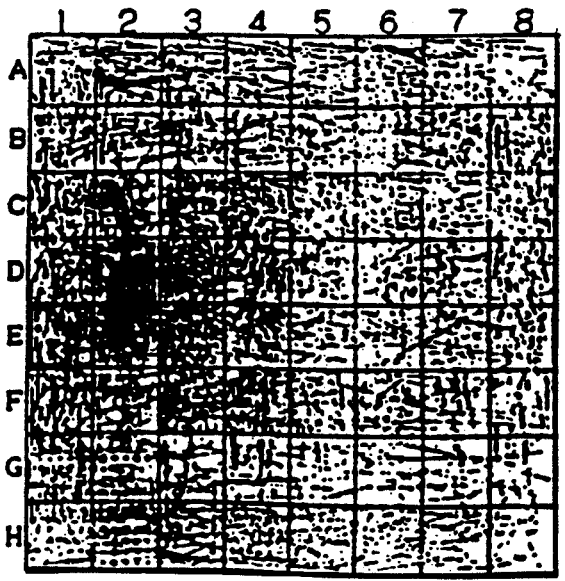
Figure 2A:
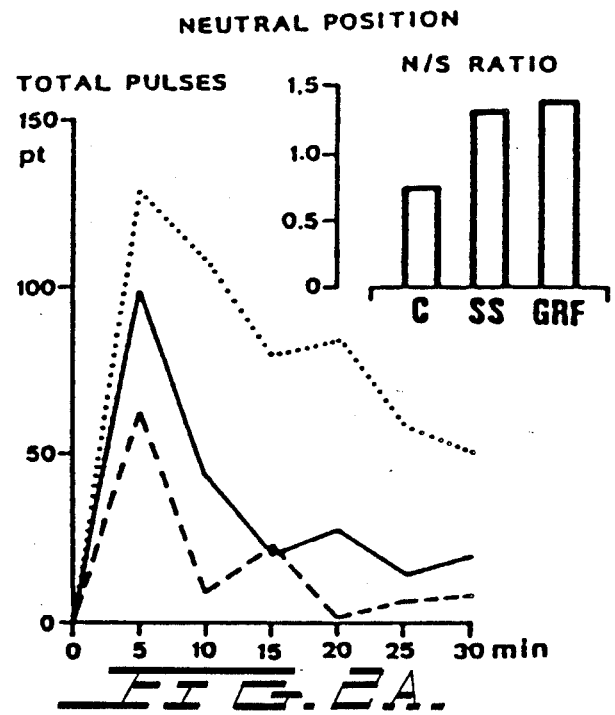
Figure 2B:
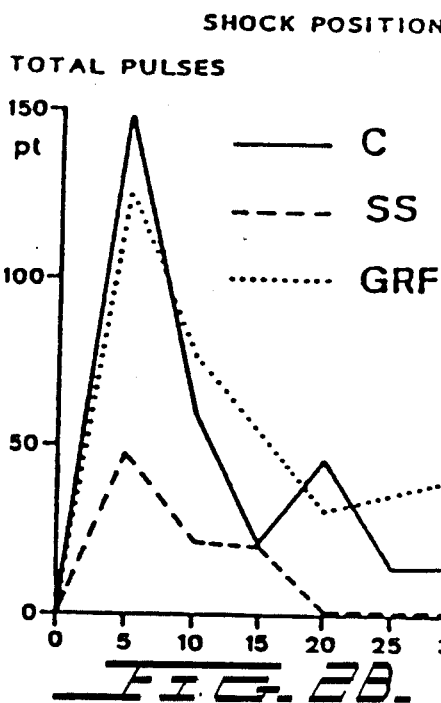
Figure 2C:
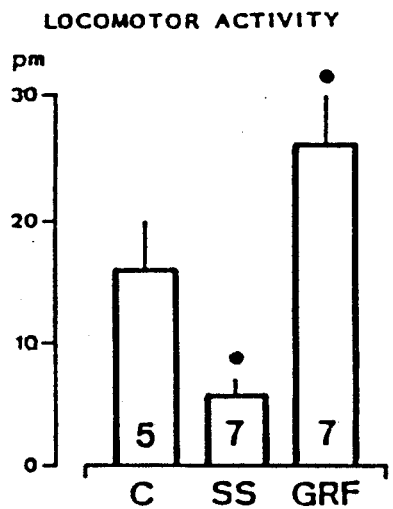
Figure 2D:
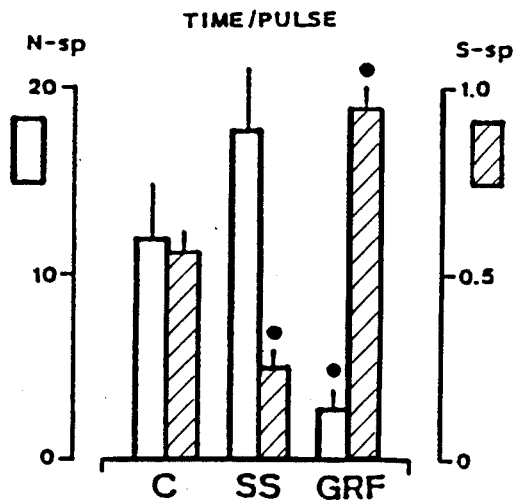
Figure 2E:
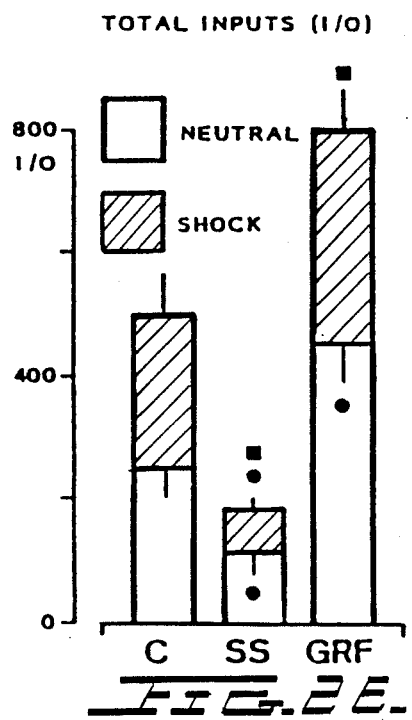
Figure 2F:
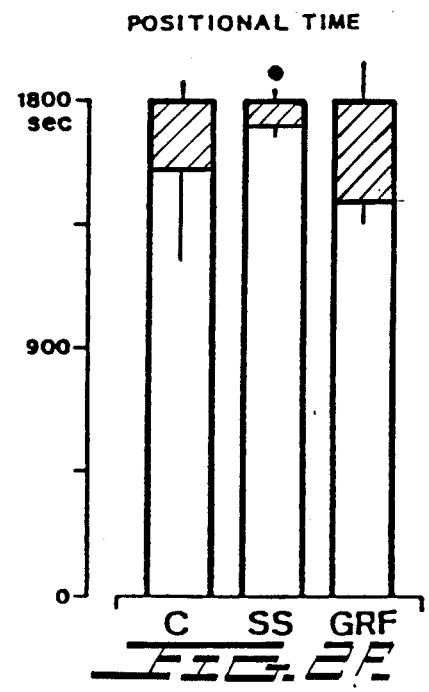
Figure 3:
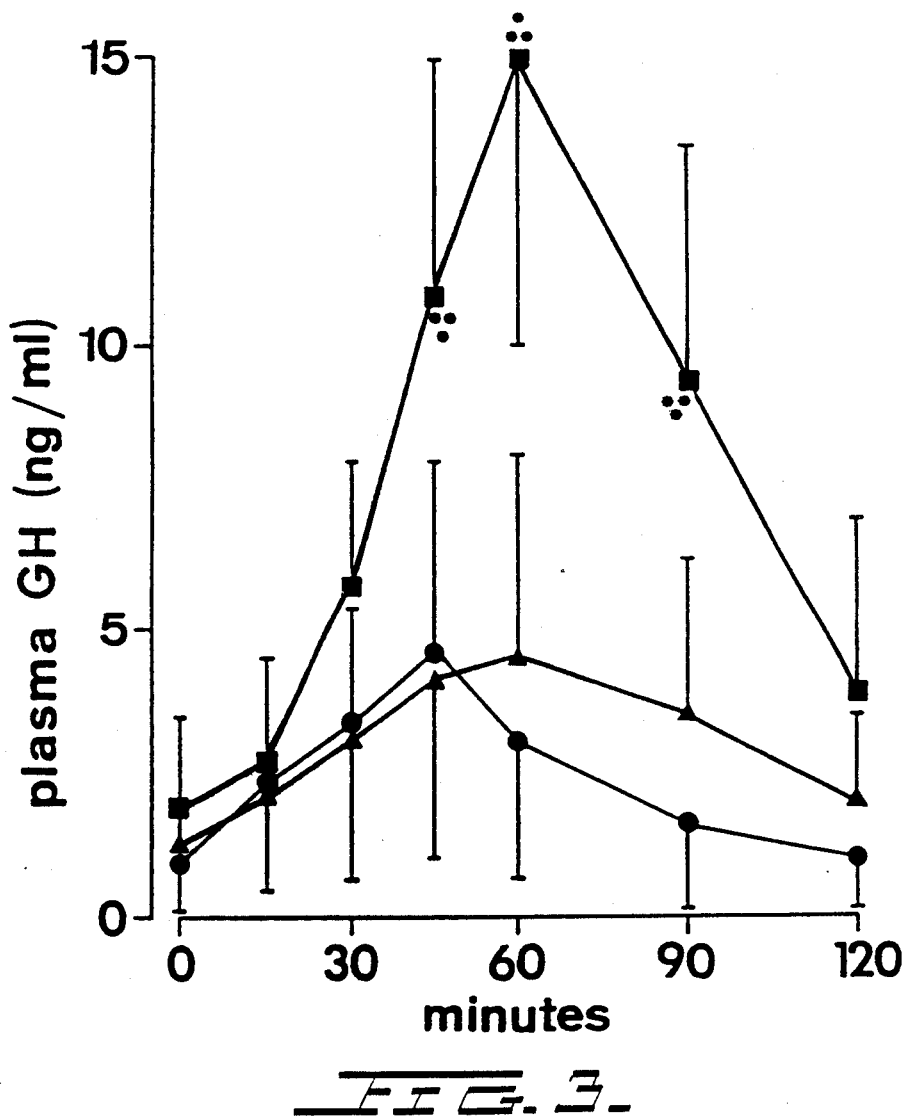

Using the maze paradigm shown in FIG. 1 in which the rats must learn to escape from the shock area in order to avoid a continuous 1.5 mA electric shock, SS (1 mcg, i.c.v.) significantly reduced LA 17.12±5.42 vs 6.01±1.45 pm, t=4.42, $p<0.005$) FIGS. 1B,3) and GRF increased LA in a dose-related manner (26.66±3.15 pm, t=3.40, $p<0.01$ at 1 mcg, FIG. 1C; and 90.2±8.4 pm, t=17.51, $p<0.005$, at 5 mcg, FIG. 1D). The amount of inputs (I/O) induced by SS was 103.5±29.5 (control =216.25±55.19, t=8.49, $p<0.005$) in the neutral area (NA) and 77.14±13.5 I/O in the shock area (SA) (control =298±40, t=1.26, n.s.). GRF generated 459.35±32.5 I/O in NA (t=18.13, $p<0.005$) and 340.5±63.5 I/O in SA (t=9.07, $p<0.005$) (FIGS. 1C,3). The NA/SA (N/S) ratios for control, SS- and GRF-treated rats were 0.72, 1.33, and 1.35, respectively (FIG. 2).

Our results clearly show that GRF and SS exert antagonistic effects on LA in novelty conditions in both open field and maze paradigms (FIGS. 1,2). If we consider the N/S ratio as in index of learning, it seems that both SS and GRF improve learning abilities at doses of approximately $6.10 \times 10^{-10}$ mol and $1.98 \times 10^{-10}$ mol, respectively.

However, since GRF induced a hyperkinetic syndrome in which the I/O rate as well as the positional time in SA were significantly higher than in the control group, it could be inferred that SS is more effective than GRF in improving learning. Indeed, the GRF-induced locomotor agitation (hyperkinetic syndrome) constitutes a serious drawback for the animal trying to differentiate and discriminate patterns in the maze (FIGS. 1C,D).

EXAMPLE 3

Twenty female in-patients with primary degenerative dementia (Alzheimer like) aged 67-84 years were divided in two therapy-groups with GRF (1-29) NH$_2$. All patients were treated with this product for 8 days with either of the following schedules:

(I) 250 mcg s.c. twice daily
(II) 50 mcg i.v. twice daily

Therapy was started after a 15-day wash-out period for psychotropic-drugs.

Evolution of patients was assessed using the MMS Folstein test and Chrichton's scale test at 12 hours, 24 hours and 7 days after starting with GRF. The statistical evaluation was made using Friedman test with a risk level p<0,01 (highly significant differences).

Both groups show a significant increase in both scores and clinical findings, more important in the group with i.v. GRF administration than in the one with s.c. administration. The effect starts at 12 hours after administration and remains significant over the whole 7 days of treatment.

The lower scores in the Crichton's scale observed for the I group are probably related with the fact that, since inclusion in either group was dependent on the difficulty of the i.v. puncture, the patients included in the s.c. group were those whose clinical situation was worst.

During the treatment with GRF the nurse in charge of the patients reported an improvement of the patient's situation regarding sphincter control and general psychomotricity. This improvement returned to pretreatment situation when the GRF administration was discontinued.

After finishing GRF administration the same groups have been evaluated with MMS-Folstein test and Crichton's scale test in order to both assess the test's reproducibility and to establish the elimination of the GRF effect thus confirming the significant effect of GRF (1-29) NH$_2$ in those patients. The variation coefficients were 12% for MMS-Folstein test and the 2.7% for Chrichton's scale test.

EXAMPLE 4

The subjects were divided into three groups:

(a) controls (N =9): 5 females and 4 males (age =70.10±2.76 years; range =66–75);

(b) inpatients with early onset senile dementia of the Alzheimer type (EOSDAT) (N =10): 5 females and 5 males (age 65.00±3.31 years; range =57–69); and (c) inpatients with late onset senile dementia of the Alzheimer type (LOSDAT) (N =10): 5 females and 5 males (age =75.70±3.77 years; range =70–82).

All the SDAT patients met the DSM-III criteria for primary degenerative dementia and rigorous diagnostic criteria for SDAT. As EOSDAT patients were considered those whose insidious memory loss or deterioration of cognitive functions began before the age of 60 and had a progressive course of more than 2 years. In LOSDAT, the onset of the disease occurred after the age of 60. The degree of severity of the dementia was assessed with Hasegawa's Dementia Rating Scale (DRS) (Hasegawa K., Inoue K. "An investigation of dementia rating scale for the elderly." Seishinigaku 16:965-969, 1974), Folstein's Mini-Mental State (MMS) Test (Folstein M. F., Folstein S., McHugh P. "Mini-mental state: a practical method for grading the cognitive state of patients for the clinician." J. Psychiat. Res. 12:189-198, 1975) and a modified model of the Brief Cognitive Rating Scale (BCRS) and Functional Assessment Stages (FAST) of Reisberg (Reisberg B., Ferris S. H., De Leon M. J. "Senile dementia of the Alzheimer type: Diagnosis and differential diagnostic features with special reference to functional assessment staging." in: Traber J., Gispen W. H. (Ed). Senile dementia of the Alzheimer type. pp 18-37, Springer-Verlag, Berlin, 1985). Concomitant pathology other than SDAT was discarded under a careful screening of the subjects with CT Scan, EEG, ECG and complementary laboratory data. Current diagnosis or history of SDM-III major affective disorder or schizophrenia as well as history of endocrine disease were criteria for exclusion. All of the control subjects were free of psychiatric and endocrine illness. All subjects included had been drug-free for a minimum of 7 days before testing.

A 21-gauge indwelling venous needle with an attached three-way stopcook was inserted into the antecubital vein. Baseline blood samples for GH determination were collected immediately before testing. GRF(1-44)NH$_2$ was then injected as an intravenous bolus (100 mcg), and blood samples were obtained at 15, 30, 45, 60, 90 and 120 minutes after injection for determination of GH concentrations in plasma. The plasma GH levels were measured by radioimmunoassay using a commercial GH-RIA-Kit (Dainabot Co. Ltd. Tokyo). The intra- and inter-assay coefficients of variation were 6.9% and 10.6%, respectively.

Simultaneously to the performance of the GRF test, electroencephalograhic and cardiovascular monitorization of the subjects were carried out. Twenty-four hours prior to the GRF test, and 3, 12, 24 and 48 hours after testing, the DRS, MMS, BCRS, and FAST tests were performed to evaluate mental performance and behavior. Additional monitoring of GRF effects was done by global physician assessment and evaluation of the Mihara Nursing Scale (MNS). This test was developed to be used as a non-cognitive parametric indicator involving several items, including quantification of food intake, locomotion, social interaction, and complementary laboratory data.

The results were analyzed statistically by the Student's test, analysis of variance (ANOVA) and the Mann-Whitney test using a NEC PC-9801VM2 computer.

GRF induced a marked increase in the levels of plasma GH in from 30 to 90 minutes after injection with a maximum peak (15.61±5.71 ng/ml, t =6.08, p <0.005) at 60 minutes in EOSDAT (FIG. 3). This response was absent in both LOSDAT and control subjects, in whom plasma GH increased slightly but never reached a significant level over basal concentrations (FIG. 3).

In the EOSDAT responders, the rise of plasma GH levels after GRF injection showed a great individual variability (range =5.5–28.75 ng/ml). This response was higher in females (19.74 ±4.86 ng.ml) than in males (11.52±2.82 ng/ml, p<0.005) (see the Table). No sexual differences were evident in the other two groups. Significant differences in the basal plasma GH concentrations among the three groups were not detected.

TABLE 1

| | | | | | | |
|---|---|---|---|---|---|---|
| SEX- AND TIME-DEPENDENT RESPONSES OF GROWTH HORMONE TO GROWTH HORMONE-RELEASING FACTOR IN PATIENTS WITH SENILE DEMENTIA AND ELDERLY SUBJECTS | | | | | | |
| TIME (min.) | CONTROL (females) | CONTROL (males) | EOSDAT (females) | EOSDAT (males) | LOSDAT (females) | LOSDAT (males) |
| 0 | 1.03 ± 0.94 | 1.07 ± 0.92 | 1.92 ± 1.52 | 1.99 ± 1.67 | 1.09 ± 1.01 | 0.95 ± 0.98 |

TABLE 1-continued

SEX- AND TIME-DEPENDENT RESPONSES OF GROWTH HORMONE TO GROWTH HORMONE-RELEASING FACTOR IN PATIENTS WITH SENILE DEMENTIA AND ELDERLY SUBJECTS

| TIME (min.) | CONTROL (females) | CONTROL (males) | EOSDAT (females) | EOSDAT (males) | LOSDAT (females) | LOSDAT (males) |
|---|---|---|---|---|---|---|
| 15 | 3.09 ± 1.58 | 2.21 ± 1.87 | 2.23 ± 1.90 | 2.70 ± 1.92 | 2.04 ± 1.01 | 2.13 ± 0.94 |
| 30 | 3.68 ± 2.09 | 3.16 ± 2.76 | 6.26 ± 2.05 | 5.49 ± 1.91 | 3.65 ± 2.35 | 2.81 ± 1.90 |
| 45 | 4.28 ± 3.38 | 5.17 ± 3.46 | 14.86 ± 3.57 | 6.87 ± 2.84* | 4.68 ± 3.18 | 3.61 ± 3.51 |
| 60 | 2.97 ± 1.96 | 3.17 ± 2.61 | 19.74 ± 4.86 | 11.52 ± 2.82** | 4.97 ± 3.86 | 4.09 ± 2.56 |
| 90 | 2.04 ± 1.38 | 1.88 ± 1.87 | 11.28 ± 5.72 | 7.41 + 2.79 | 3.04 ± 3.22 | 3.08 ± 2.22 |
| 120 | 1.10 ± 0.95 | 0.91 ± 0.87 | 5.09 ± 3.01 | 2.73 ± 1.71 | 2.44 ± 2.05 | 1.64 ± 0.82 |
| N | 5 | 4 | 5 | 5 | 5 | 5 |
| AGE | 70.20 ± 2.78 | 70.00 ± 2.73 | 65.00 ± 4.25 | 65.00 ± 2.00 | 76.20 ± 4.48 | 75.20 ± 2.00 |
| RANGE | 67–75 | 66–73 | 57–69 | 62–68 | 70–82 | 73–80 |
| STAGE | I-II | I-II | VI-VII | V-VII | VI-VII | VI-VII |

EOSDAT = Early Onset Senile Dementia of the Alzheimer Type
LOSDAT = Late Onset Senile Dementia of the Alzheimer Type
*p < 0.01 vs. females
**p < 0.005 vs. females EEG was abnomal in 95% of SDAT patients due to the advanced stage of the disease. Basic electroencephalographic patterns for controls (N =6) and SDAT subjects (N =7, prior to the GRF test were 9.27±0.11 Hz/47.36±3.36 uV and 8.08±0.67 Hz/40.80±6.06 uV, respectively. Global EEG evaluation after testing yielded a basic rhythm of 9.05±0.12 Hz (p<0.025)/49.67±5.75 uV for controls and 7.46±0.53 Hz/43.69±5.12 uV for SDAT. Sequential EEG analysis revealed a fall in frequency (8.75±0.25 Hz, p<0.005) and an increase in amplitude (55.60±6.40 uV, p<0.02) in control subjects and in SDAT patients (7.05±0.90 Hz, p<0.05/52.5±9.89 uV, p<0.005) in from 15 to 45 minutes after injection, preceding the maximum plasma GH peak.

There was a good correlation of scores between the DRS and MMS tests. Basal scores for DRS/MMS prior to the GRF test were 3.5±1.75/3.5±2.65. After testing, scores increased to 5.5±2.10/5.15±3.75 (3 hr), 6.75±3.25/5.5±3.65 (12 hr), 4.35±1.95/4.5±2.75 (24 hr), and 3.5±1.55/4.35±2.75 (48 hr).

Figure 4:
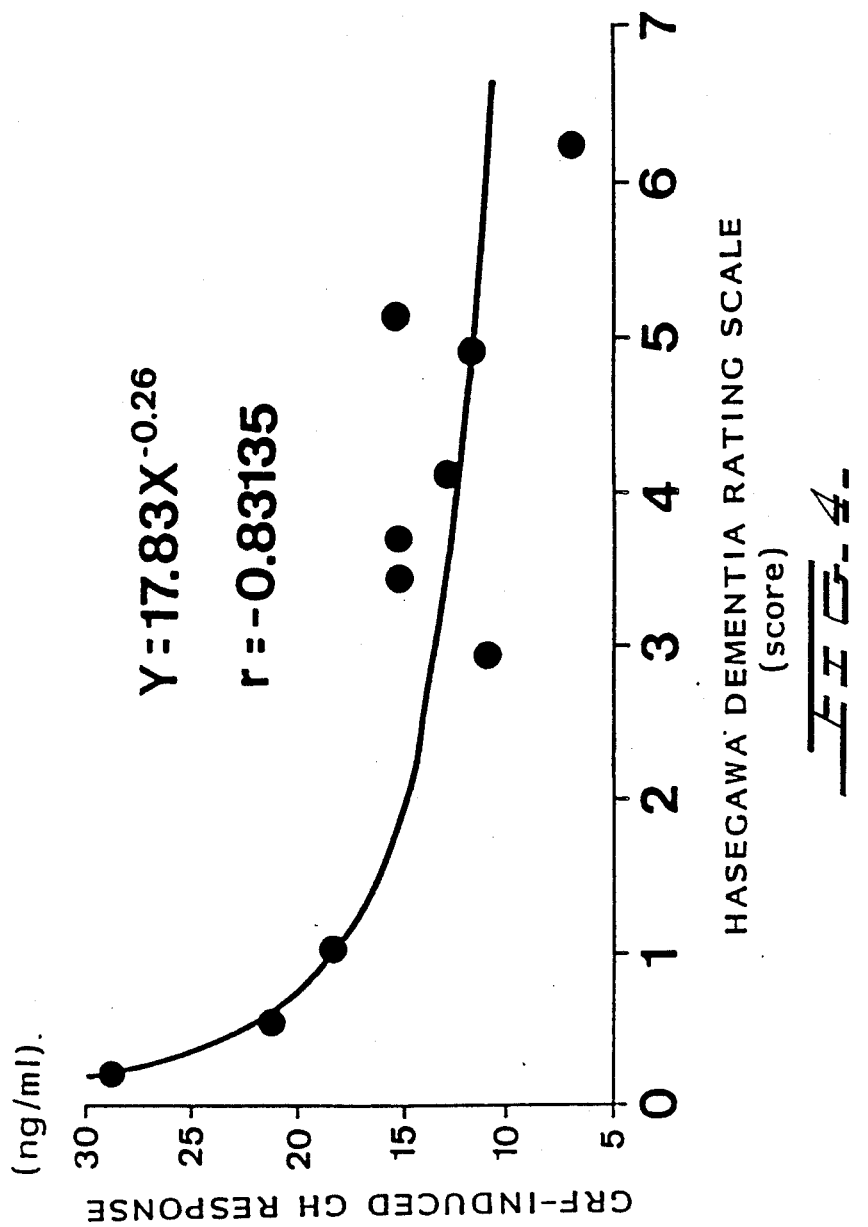

Although these differences were not statistically significant, they were clinically relevant. An inverse curvilinear relationship (Fig.4) between the variables mental performance (x) and maximum GH response to GRF at 60 minutes (y) was observed (r = −0.83). A careful evaluation of the BCRS showed that the axes more significantly affected by GRF were Axis 4 (orientation, 30%), Axis 7 (psychomotor, 50%), and Axis 8 (mood and behavior, 40%). According to the MNS, appetite increased in 45% of the patients and in 30% of the controls (2 patients developed a bulimic syndrome), and social interaction improved in 40% of the patients. All these behaviors were transient.

These results demonstrate that GRF induces a significant increase of the plasma GH levels 60 minutes after injection in EOSDAT. This GH response is about 15 minutes delayed with respect to the small peak observed in control subjects. Furhtermore, the GRF-induced GH response slightly correlates with the severity of the disease and is accompanied by EEG and behavioral changes mainly circumscribed to psychomotor functions.

Reasonable variations, such as those which would occur to a skilled artisan, can be made herein without departing from the scope of the invention.

What is claimed is:

1. A method of detecting early onset senile dementia of the Alzheimer type in a subject comprising administering to that subject an effective amount of growth hormone releasing factor and monitoring the growth hormone response thereto, whereby an elevated response versus normal controls is indicative of early onset senile dementia of the Alzheimer type.

2. The method of claim 1 wherein
about 1 to about 10 mcg/kg (i.v.) or about 5 to about 50 mcg/kg (s.c.) of growth hormone releasing factor.

3. The method of claim 2, wherein the growth hormone releasing factor is $GRF_{1-29}$.

4. The method of claim 2, wherein the growth hormone releasing factor is $GRF_{1-44}$.

* * * * *

UNITED STATES PATENT AND TRADEMARK OFFICE
CERTIFICATE OF CORRECTION

PATENT NO.   : 4,939,124
DATED        : July 3, 1990
INVENTOR(S)  : Ramon Cacabelos It is certified that error appears in the above-identified patent and that said Letters Patent is hereby corrected as shown below:

Col. 8, line 46 "tor" should read --tor is administered--.

Signed and Sealed this

Eighth Day of December, 1992

Attest:

DOUGLAS B. COMER

Attesting Officer                Acting Commissioner of Patents and Trademarks